United States Patent [19]

Mitchell

[11] Patent Number: 5,136,079
[45] Date of Patent: Aug. 4, 1992

[54] REGIOSELECTIVE SYNTHESIS

[75] Inventor: David Mitchell, Indianapolis, Ind.

[73] Assignee: Eli Lilly and Company, Indianapolis, Ind.

[21] Appl. No.: 661,277

[22] Filed: Feb. 26, 1991

[51] Int. Cl.$^5$ ............... C07C 253/16; C07D 333/12; C07D 333/16; C07D 307/42
[52] U.S. Cl. ................... 558/347; 546/330; 548/205; 549/75; 549/491
[58] Field of Search ............ 558/347; 549/75, 491; 546/330; 548/205

[56] References Cited

U.S. PATENT DOCUMENTS

| | | | |
|---|---|---|---|
| 3,395,172 | 7/1968 | Schweter | 558/347 |
| 3,839,399 | 10/1974 | Starks et al. | 558/344 X |
| 3,862,204 | 1/1975 | Umbach et al. | 558/347 |
| 3,992,432 | 11/1976 | Napier et al. | 558/344 |
| 4,070,394 | 1/1978 | Wiegand | 558/347 |
| 4,314,081 | 2/1982 | Molloy et al. | 564/347 |
| 4,956,388 | 9/1990 | Robertson et al. | 514/651 |

FOREIGN PATENT DOCUMENTS

| | | | |
|---|---|---|---|
| 572502 | 3/1959 | Canada | 558/347 |
| 369685 | 5/1990 | European Pat. Off. | |
| 577686 | 3/1930 | Fed. Rep. of Germany | 558/347 |
| 41-16504 | 9/1966 | Japan | 558/347 |

OTHER PUBLICATIONS

Koenig, et al., *Tetrahedron Letters*, 26, (1974); pp. 2275-2278.
Chiba, et al., *Synthesis*, (1990); pp. 209-211.
Sassaman, et al., *J. Org. Chem.*, 55, (1990); pp. 2016-2018.

*Primary Examiner*—Joseph Paul Brust
*Attorney, Agent, or Firm*—Joseph A. Jones; Leroy Whitaker; Robert A. Conrad

[57] ABSTRACT

This invention provides a process for preparing 3-substituted-3-hydroxypropanenitriles.

10 Claims, No Drawings

REGIOSELECTIVE SYNTHESIS

BACKGROUND OF THE INVENTION

3-Substituted-3-aryloxypropanamines are known in the art to be useful as medicinal agents by virtue of their action of inhibiting the reuptake of serotonin or norepinephrine. See, e.g., U.S. Pat. Nos. 4,314,081 and 4,956,388. The preferred characteristics of particular enantiomers over their racemates is also known—see, e.g., U.S. Pat. No. 4,956,388 and EPO Patent Application Publication 369,685.

This invention provides a method for converting an epoxide intermediate into a 3-substituted-3-hydroxypropanenitrile which can be used in the synthesis of the aforementioned pharmaceutical agents.

SUMMARY OF THE INVENTION

This invention provides a process for preparing a compound of Formula I

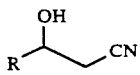   I wherein R is phenyl, $C_5$-$C_7$ cycloalkyl, thienyl, halothienyl, ($C_1$-$C_4$)alkylthienyl, furanyl, pyridyl, or thiazolyl, which comprises allowing an epoxide of the Formula II

   II to react with an alkali metal cyanide in the presence of a phase transfer catalyst in an biphasic mixture of water and a water immiscible solvent.

DETAILED DESCRIPTION AND PREFERRED EMBODIMENT

The compounds of Formula I are intermediates for preparing 3-substituted-3-aryloxypropanamines as described in U.S. Pat. Nos. 4,314,081 and 4,956,388, which references are expressly incorporated into this specification. The intermediates of Formula I can be reacted with reagent of the formula Ar-Y where Y is a leaving group such as p-toluenesulfonyl, methanesulfonyl, triphenylphosphine oxide, halo, and the like and Ar is an optionally substituted phenyl or naphthyl group as described in the two cited U.S. patents. The resulting 3-substituted-3-aryloxypropanenitrile can then be reduced to the primary amine by standard methods and optionally alkylated to provide secondary or tertiary amines, all of which are medicinal agents as described in the cited patents. Alternatively, the intermediates of Formula I can be first reduced to the primary amine and then alkylated with Ar-Y as described above.

The preferred application of the process of this invention relates to those compounds where R is phenyl. Thus, in the preferred embodiment of this invention, the compound of Formula II is commercially available (R)-styrene oxide. Other related intermediates II are either commercially available or are prepared by literature methods.

The compounds of Formula I possess one chiral carbon atom, i.e., the atom to which the aryl and hydroxy groups are attached. The corresponding epoxide precursor II likewise has the same chiral atom. The reaction of this process is regio-selective in that the addition of the cyanide to the epoxide proceeds such that the only product is the 3-substituted-3-hydroxypropanenitrile I with no 3-hydroxy-1-substituted-propanenitrile being observed. However, this reaction does not induce any stereoselectivity preferentially forming one of the enantiomers of Formula I. Thus, employing racemic epoxide II results in the formations of racemic I; employing a chiral epoxide II results in the formation of only the one corresponding enantiomer of Formula I.

The alkali metal cyanides are ionic cyanide reagents wherein the cation is an alkali metal ion. Preferred alkali metals cyanides are sodium cyanide and potassium cyanide. The term "phase transfer catalyst" as used in this application refers to a catalyst which is capable of carrying a nucleophile from an aqueous phase into an organic phase. See, e.g., "Advanced Organic Chemistry", Jerry March, ed (Third Edition, John Wiley and Sons, Inc. 1985) pp. 320–322. Suitable phase transfer catalysts include quaternary ammonium or phosphonium salts, crown ethers and cryptands. The preferred phase transfer catalyst to be employed will depend upon the particular alkali metal cation and organic solvent which is employed. Preferred transfer catalyst are the quaternary ammonium salts, particularly tetralkylammonium halides, such as tetrabutylammonium bromide. Other such phase transfer catalysts are well known in the literature. See, e.g., *Aldrichimic Acta*, 13 (3), 55 (1980).

Suitable water immiscible solvents are those which are neither soluble with the aqueous layer nor are reactive in presence of either the epoxide II or the alkali metal cyanide. Such solvents include haloalkanes, such as methylene chloride, 1,2-dichloroethane, and the like, and other solvents such as ethers (e.g., diethyl ether, tetrahydrofuran, dimethoxyethane), aromatics (e.g., benzene, toluene), and hydrocarbons (e.g., heptane, hexane, pentane, petroleum ether, and the like).

The reaction is best accomplished at temperatures above room temperature, particularly at temperatures from about 40° C. up to the reflux temperature of the reaction mixture.

In addition, it is preferred that the pH of the aqueous layer be neutral to basic, i.e., above pH 7, and preferably below pH 10. Thus, a preferred reaction condition is where a water soluble base, particularly an alkali metal hydroxide, is added in a sufficient quantity to the aqueous layer of the biphasic mixture to render the pH 7–10. This may be best accomplished by using 1 or 2N potassium hydroxide or sodium hydroxide instead of pure water in the biphasic mixture.

The reaction is best carried out when the ratio of water immiscible solvent to water is from 1:1 to 4:1 by volume. Similarly, it is preferred that a slight molar excess of the alkali metal cyanide is present relative to the amount of epoxide II. A preferred ratio would be at least about a 10% molar excess of the cyanide to the epoxide reagent. The amount of phase transfer catalyst present can also vary. However, it is preferred that the phase transfer reagent be present in a 1% to 10% molar amount relative to the amount of epoxide II.

Thus, under the preferred reaction conditions, 1 molar equivalent of epoxide II, 1.1 molar equivalents of potassium cyanide, and 0.1 molar equivalents of tetrabutylammonium bromide are allowed to heat at reflex in 4 volumes (volume/gram of epoxide II) 1,2-dichloroethane and 1 volume of 1N potassium hydroxide solution. After heating for 6 hours at reflux, the mixture is cooled to room temperature, diluted with 1N potassium hydroxide solution and extracted with methylene chloride. The organic extracts are dried over magnesium sulfate and concentrated in vacuo to provide the desired intermediated II which can be further purified by distillation or other means.

The following experiments further illustrate the process of this invention. These examples are illustrative only are not intended to limit the scope of the invention.

EXPERIMENT 1

Preparation of (S)-3-phenyl-3-hydroxypropanenitrile

To a 250 round bottom flask were sequentially added 10.0 g of (R)-styrene oxide, 40 ml of 1,2-dichloroethane, 40 ml of 1N potassium hydroxide, 5.96 g of potassium cyanide and 267 mg of tetrabutylammonium bromide. The resulting mixture was heated at reflux for 6 hours. The reaction mixture was cooled and diluted with 1N potassium hydroxide, and extracted with diethyl ether. The ether extracts were combined and washed twice with a saturated sodium chloride solution. The organics layer was dried over magnesium sulfate and concentrated in vacuo. The resulting yellow oil was vacuum distilled at 13 mm pressure and the distillate collected at 140°-180° C. providing 4.11 g of title intermediate.

IR (neat): 3445, 3065, 3034, 2899, 2255, 1604, 1495, 1456, 1412, 1329, 1204, 1087, 1058, 1028, 940, 868, 757, 703 cm$^{-1}$;

$^1$H NMR (300 MHz, CDCl$_3$) δ7.36 (m, 5H), 4.98 (t, J=6.11 Hz, 1H), 3.13 (br s, 1H), 2.71 (d, J=6.09 Hz, 2H);

$^{13}$C NMR (300 MHz, CDCl$_3$) δ27.86, 69.87, 117.49, 125.59, 128.70, 128.87, 141.16.

Analysis for C$_9$H$_9$NO: Calc: C, 73.45; H, 6.16; N, 9.52; Found: C, 73.66; H, 6.30; N, 9.70.

EXPERIMENT 2

Preparation of 3-phenyl-3-hydroxypropanenitrile

The procedure of Experiment 1 was repeated employing 1.0 g of racemic styrene oxide, 4 ml of 1,2-dichloroethane, 2 ml of water, 596 mg of potassium cyanide, and 267 mg of tetrabutylammonium bromide. After 6 hours of heating at reflux, the reaction mixture was cooled and worked up extracting with methylene chloride. Proton nuclear magnetic resonance analysis indicated the desired product contaminated with the phase transfer catalyst.

EXPERIMENT 3

Experiment 2 was repeated except that 1 ml of 1N potassium hydroxide solution was used in place of the water. The isolated intermediate was also contaminated with phase transfer reagent.

EXPERIMENT 4

Experiment 2 was repeated replacing the 2 ml of water with 4 ml of 2N potassium hydroxide solution. The reaction was heated at reflux for 24 hours and worked up. Proton nuclear magnetic resonance indicated the desired product.

EXPERIMENT 5

The procedure of Experiment 1 was repeated replacing the 40 ml of potassium hydroxide solution with 40 ml of water to which 5 grams of sodium bicarbonate had been added. The reaction was worked up in the same way. The isolated oil was identified by proton nuclear magnetic resonance to be the desired product contaminated with styrene oxide starting material.

EXPERIMENT 6

The reaction of Experiment 1 was repeated with racemic styrene oxide (1.0 g) and 400 mg of 18-crown 6 as the catalyst in place of the tetrabutylammonium bromide. The result was 622 mg of racemic 3-phenyl-3-hydroxypropanenitrile.

IR (neat): 3445, 3065, 3034, 2899, 2255, 1604, 1495, 1456, 1412, 1329, 1204, 1087, 1058, 1028, 940, 868, 757, 703 cm$^{-1}$;

$^1$H NMR (300 MHz, CDCl$_3$) δ7.36 (m, 5H), 4.98 (t, J=6.11 Hz, 1H), 3.13 (br s, 1H), 2.71 (d, J=6.09 Hz, 2H);

$^{13}$C NMR (300 MHz, CDCl$_3$) δ27.86, 69.87, 117.49, 125.59, 128.70, 128.87, 141.16;

Analysis for C$_9$H$_9$NO; Calc: C, 73.45; H, 6.16; N, 9.52; Found: C, 73.17; H, 6.13; N, 9.24.

I claim:

1. A regiospecific process for preparing a compound of Formula I

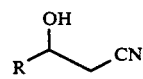

wherein R is phenyl, C$_5$-C$_7$ cycloalkyl, thienyl, halothienyl, (C$_1$-C$_4$)alkylthienyl, furanyl, pyridyl, or thiazolyl, which comprises allowing an epoxide of the formula II

to react with an alkali metal cyanide in the presence of a phase transfer catalyst in a biphasic mixture of water and a water immiscible solvent.

2. The process of claim 1 wherein the pH of the water layer is basic.

3. The process of claim 2 wherein the alkali metal cyanide is potassium cyanide or sodium cyanide.

4. The process of claim 3 wherein the water immiscible solvent is 1,2-dichloroethane.

5. The process of claim 4 wherein the phase transfer catalyst is tetrabutylammonium bromide.

6. The process of claim 1 wherein R is phenyl.

7. The process of claim 1 wherein the produce is the regiospecific compound of formula

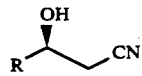

8. The process of claim 1 wherein the product is the regiospecific racemic mixture of formula

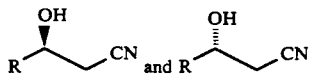

9. A process for preparing a compound of Formula I

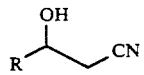

wherein R is phenyl which comprises allowing an epoxide of the Formula II

to react with potassium cyanide or sodium cyanide in the presence of tetrabutylammonium bromide in a biphasic mixture of water and 1,2-dichloroethane.

10. A process for preparing a compound of Formula I

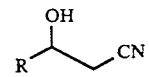

wherein R is phenyl which comprises allowing an epoxide of the Formula II

to react with potassium cyanide in the presence of tetrabutylammonium bromide in a biphasic mixture of water and 1,2-dichloroethane.

* * * * *